US011849792B2

(12) United States Patent
Hashimoto et al.

(10) Patent No.: US 11,849,792 B2
(45) Date of Patent: Dec. 26, 2023

(54) HEAD-MOUNTED DEVICE, HEAT STROKE PREVENTION SYSTEM, AND REHYDRATION WARNING SYSTEM

(71) Applicants: Public University Corporation Suwa University of Science Foundation, Nagano (JP); Fujita Corporation, Tokyo (JP)

(72) Inventors: Nobuaki Hashimoto, Nagano (JP); Yoshinori Kumita, Tokyo (JP); Toshihito Kondo, Tokyo (JP)

(73) Assignees: Public University Corporation Suwa University of Science Foundation, Nagano (JP); Fujita Corporation, Tokyo (JP)

( * ) Notice: Subject to any disclaimer, the term of this patent is extended or adjusted under 35 U.S.C. 154(b) by 311 days.

(21) Appl. No.: 17/434,845

(22) PCT Filed: Mar. 12, 2020

(86) PCT No.: PCT/JP2020/010963
§ 371 (c)(1),
(2) Date: Aug. 30, 2021

(87) PCT Pub. No.: WO2020/184687
PCT Pub. Date: Sep. 17, 2020

(65) Prior Publication Data
US 2022/0142283 A1    May 12, 2022

(30) Foreign Application Priority Data
Mar. 13, 2019  (JP) .................................. 2019-046034

(51) Int. Cl.
*A42B 3/04*   (2006.01)
*A42B 1/242*  (2021.01)
(Continued)

(52) U.S. Cl.
CPC ............ *A42B 3/0433* (2013.01); *A42B 1/242* (2013.01); *A42B 3/28* (2013.01); *A61B 5/0002* (2013.01);
(Continued)

(58) Field of Classification Search
CPC ....... A42B 3/286; A42B 3/283; A42B 3/0433; A42B 1/242; A42B 3/28
See application file for complete search history.

(56) References Cited

U.S. PATENT DOCUMENTS 6,989,605 B2 * 1/2006 Hashimoto ......... H01L 23/3114
                                                    257/E25.011
11,122,849 B2 * 9/2021 Hashimoto ............ A42B 3/283
(Continued)

FOREIGN PATENT DOCUMENTS

CN    201860845 U    6/2011
CN    105595976 A    5/2016
(Continued)

OTHER PUBLICATIONS

Chinese Office Action for corresponding Chinese Application No. 202080020438.x dated Jun. 8, 2022.
(Continued)

*Primary Examiner* — Khaled Annis
(74) *Attorney, Agent, or Firm* — ArentFox Schiff LLP; Michael Fainberg

(57) ABSTRACT

A head-mounted device capable of more highly accurately measuring the physical conditions of a wearer as a worker that are necessary for estimating the possibility of heat stroke is provided. A head-mounted device includes an outer shell; a first channel as a gap between a head of a wearer and the outer shell; a second channel provided in the outer shell and connected to the first channel; a fan configured to send air from one of the first channel and the second channel to
(Continued)

the other; a salinity sensor configured to measure salt concentration of sweat of the wearer; a first humidity sensor configured to measure an absolute humidity of intake air entering one of the first channel and the second channel; and a second humidity sensor configured to measure an absolute humidity of exhaust air exiting from the other of the first channel and the second channel.

16 Claims, 6 Drawing Sheets

(51) Int. Cl.
*A42B 3/28* (2006.01)
*A61B 5/00* (2006.01)
*A61B 5/0205* (2006.01)
*A61B 5/024* (2006.01)
*A61B 5/145* (2006.01)
*G08B 21/02* (2006.01)

(52) U.S. Cl.
CPC ...... *A61B 5/02055* (2013.01); *A61B 5/02438* (2013.01); *A61B 5/14517* (2013.01); *A61B 5/14546* (2013.01); *A61B 5/4266* (2013.01); *A61B 5/6803* (2013.01); *A61B 5/746* (2013.01); *G08B 21/02* (2013.01); *A61B 2560/0252* (2013.01); *A61B 2562/029* (2013.01); *A61B 2562/0271* (2013.01); *A61B 2562/04* (2013.01); *A61B 2562/06* (2013.01)

(56) References Cited

U.S. PATENT DOCUMENTS

| | | | | |
|---|---|---|---|---|
| 2021/0022430 | A1* | 1/2021 | Hashimoto | ............ A42B 3/046 |
| 2022/0142283 | A1* | 5/2022 | Hashimoto | .......... A42B 3/0433 |

FOREIGN PATENT DOCUMENTS

| | | | |
|---|---|---|---|
| JP | 3-286919 | A | 12/1991 |
| JP | 2005-112983 | A | 4/2002 |
| JP | 2016-37671 | A | 3/2016 |
| JP | 2016-132835 | A | 7/2016 |
| JP | 2016-126440 | A | 11/2016 |
| JP | 2017-115275 | A | 6/2017 |
| JP | 2014-134905 | A | 7/2017 |
| JP | 2017-153576 | A | 9/2017 |
| JP | 2017-214673 | A | 12/2017 |
| WO | 2018/110457 | A1 | 6/2018 |
| WO | WO-2020184686 | A1 * | 9/2020 |

OTHER PUBLICATIONS

"Lets Prevent Heat Stroke", Ministry of Health, Labour and Welfare, Labour Standards Bureau, Apr. 2013.
"Lets Prevent Heat Stroke at Work" Tokyo Labor Bureau, Feb. 2017.

* cited by examiner

HEAD-MOUNTED DEVICE, HEAT STROKE PREVENTION SYSTEM, AND REHYDRATION WARNING SYSTEM

CROSS-REFERENCE TO RELATED APPLICATION

This application is a national stage application of International Application No. PCT/JP2020/010963, filed on Mar. 12 2020, which claims priority to Japanese application 2019-046034 filed on Mar. 13, 2019 and is incorporated by reference herein in its entirety.

FIELD

The present disclosure relates to a head-mounted device, a heat stroke prevention system, and a rehydration warning system.

BACKGROUND

At construction sites, workers may work under high temperature environments. Under high temperature environments, it is necessary to prevent heat stroke of workers. Conventionally, devices to be worn by workers in order to prevent heat stroke have been known. For example, Patent Literature 1 describes a helmet provided with a temperature sensor and a humidity sensor. The helmet in Patent Literature 1 enables a manager to grasp the situations inside the helmet, and hence when an abnormality occurs, the manager can contact a worker. Non Patent Literature 1 describes signs that it is necessary to stop exposure to heat. Non Patent Literature 2 describes symptoms of heat stroke.

CITATION LIST

Patent Literature

Patent Literature 1: Japanese Patent Application Laid-open No. 2017-115275
Non Patent Literature 1: "Let's Prevent Heat Stroke", Ministry of Health, Labour and Welfare, Labour Standards Bureau, Prefectural Labour Bureau, Labour Standards Supervision Office, April 2013.
Non Patent Literature 2: ""Let's Prevent Heat Stroke at Work", Tokyo Labor Bureau Health Service Division, February 2017.

SUMMARY

Technical Problem

The helmet in Patent Literature 1, however, simply measures the temperature and the humidity inside the helmet. Thus, there is a limit to accurate detection of the physical conditions of a wearer as a worker that are necessary for estimating the possibility of heat stroke, particularly such as an amount of decrease in the amount of water and salt in the body of the worker. Therefore, it is difficult to improve the accuracy of estimation of the possibility of heat stroke.

The present disclosure has been made in view of the above-mentioned problem and has an object to provide a head-mounted device capable of more highly accurately measuring the physical conditions of a wearer as a worker that are necessary for estimating the possibility of heat stroke.

Solution to Problem

To achieve the above-described object, a head-mounted device according to an aspect of the present disclosure includes an outer shell; a first channel as a gap between a head of a wearer and the outer shell; a second channel provided in the outer shell and connected to the first channel; a fan configured to send air from one of the first channel and the second channel to the other; a salinity sensor configured to measure salt concentration of sweat of the wearer; a first humidity sensor configured to measure an absolute humidity of intake air entering one of the first channel and the second channel; and a second humidity sensor configured to measure an absolute humidity of exhaust air exiting from the other of the first channel and the second channel.

As a preferred aspect of the head-mounted device, the fan sends air with an air volume with which a temperature of the exhaust air becomes equal to or higher than a dew-point temperature of the exhaust air.

As a preferred aspect of the head-mounted device, the first humidity sensor is located on outside of the outer shell.

As a preferred aspect of the head-mounted device, the first humidity sensor measures a temperature and a relative humidity of the intake air, and is located on an inner surface of the outer shell.

As a preferred aspect of the head-mounted device, the fan sends air from the first channel toward the second channel and is located at a downstream end portion of the first channel, and the second humidity sensor is located downstream of the fan.

As a preferred aspect of the head-mounted device, the head-mounted device includes a sensor unit. The sensor unit includes a housing; a tube member having one end connected to the housing and another end disposed inside the outer shell; the fan; the salinity sensor; the first humidity sensor; and the second humidity sensor. The tube member, the fan, the salinity sensor, the first humidity sensor, and the second humidity sensor are supported by the housing.

As a preferred aspect of the head-mounted device, the sensor unit is detachable from the outer shell.

As a preferred aspect of the head-mounted device, the head-mounted device includes a body temperature sensor configured to measure a body temperature of the wearer.

As a preferred aspect of the head-mounted device, the body temperature sensor measures a deep body temperature.

As a preferred aspect of the head-mounted device, the head-mounted device includes a heartbeat sensor configured to measure a heart rate of the wearer.

As a preferred aspect of the head-mounted device, the head-mounted device includes an environmental sensor configured to measure a wet-bulb temperature and a black-bulb temperature around the wearer.

As a preferred aspect of the head-mounted device, the head-mounted device includes an airflow measurement device configured to measure an air volume of the fan.

As a preferred aspect of the head-mounted device, the airflow measurement device is an airflow sensor provided at an air inlet or an outlet of the fan.

As a preferred aspect of the head-mounted device, the airflow measurement device includes a pressure sensor configured to measure a differential pressure of the fan, and the heat-mounted device includes a control device configured to calculate the air volume of the fan based on information obtained from the pressure sensor.

As a preferred aspect of the head-mounted device, the airflow measurement device includes a detection mechanism configured to detect power supply voltage that drives the fan, and the head-mounted device includes a control device configured to calculate the air volume of the fan based on information obtained from the detection mechanism.

As a preferred aspect of the head-mounted device, the head-mounted device includes a control device configured to calculate an amount of sweating and an amount of salt loss of the wearer based on information obtained from the salinity sensor, the first humidity sensor, and the second humidity sensor; and an alarm device configured to issue an alarm when a transition of the amount of sweating satisfies a predetermined condition.

A heat stroke prevention system according to an aspect of the present disclosure includes the above-described head-mounted device; and a management device. The head-mounted device includes a communication device configured to transmit, through wireless communication, information obtained from the salinity sensor, the first humidity sensor, and the second humidity sensor. The management device receives the information from the communication device and stores the amount of sweating and the amount of salt loss of the wearer.

As a preferred aspect of the heat stroke prevention system, the heat stroke prevention system includes an alarm device configured to issue an alarm to a manager when a transition of at least one of the amount of sweating and the amount of salt loss satisfies a predetermined condition.

As a preferred aspect of the heat stroke prevention system, the head-mounted device includes an alarm device configured to issue an alarm to the wearer when a transition of at least one of the amount of sweating and the amount of salt loss satisfies a predetermined condition.

A rehydration warning system according to an aspect of the present disclosure includes the above-described head-mounted device; and a management device. The head-mounted device includes a communication device configured to transmit, through wireless communication, information obtained from the salinity sensor, the first humidity sensor, and the second humidity sensor. The management device receives the information from the communication device and stores the amount of sweating and the amount of salt loss of the wearer.

As a preferred aspect of the rehydration warning system, the rehydration warning system includes an alarm device configured to issue an alarm to a manager when a transition of at least one of the amount of sweating and the amount of salt loss satisfies a predetermined condition.

As a preferred aspect of the rehydration warning system, the head-mounted device includes an alarm device configured to issue an alarm to the wearer when a transition of at least one of the amount of sweating and the amount of salt loss satisfies a predetermined condition.

Advantageous Effects of Invention

According to the present disclosure, the head-mounted device capable of more highly accurately measuring the physical conditions of a wearer as a worker that are necessary for estimating the possibility of heat stroke can be provided.

DESCRIPTION OF EMBODIMENTS

The present disclosure is described in detail below with reference to the drawings. The present disclosure is not limited by modes for embodying the present disclosure (hereinafter referred to as "embodiments"). Components in the following embodiments include the ones that can be easily conceived by a person skilled in the art and the ones that are substantially the same, that is, the ones in the range of equivalents. Furthermore, the components disclosed in the following embodiments can be combined as appropriate.

EMBODIMENT

Figure 1:
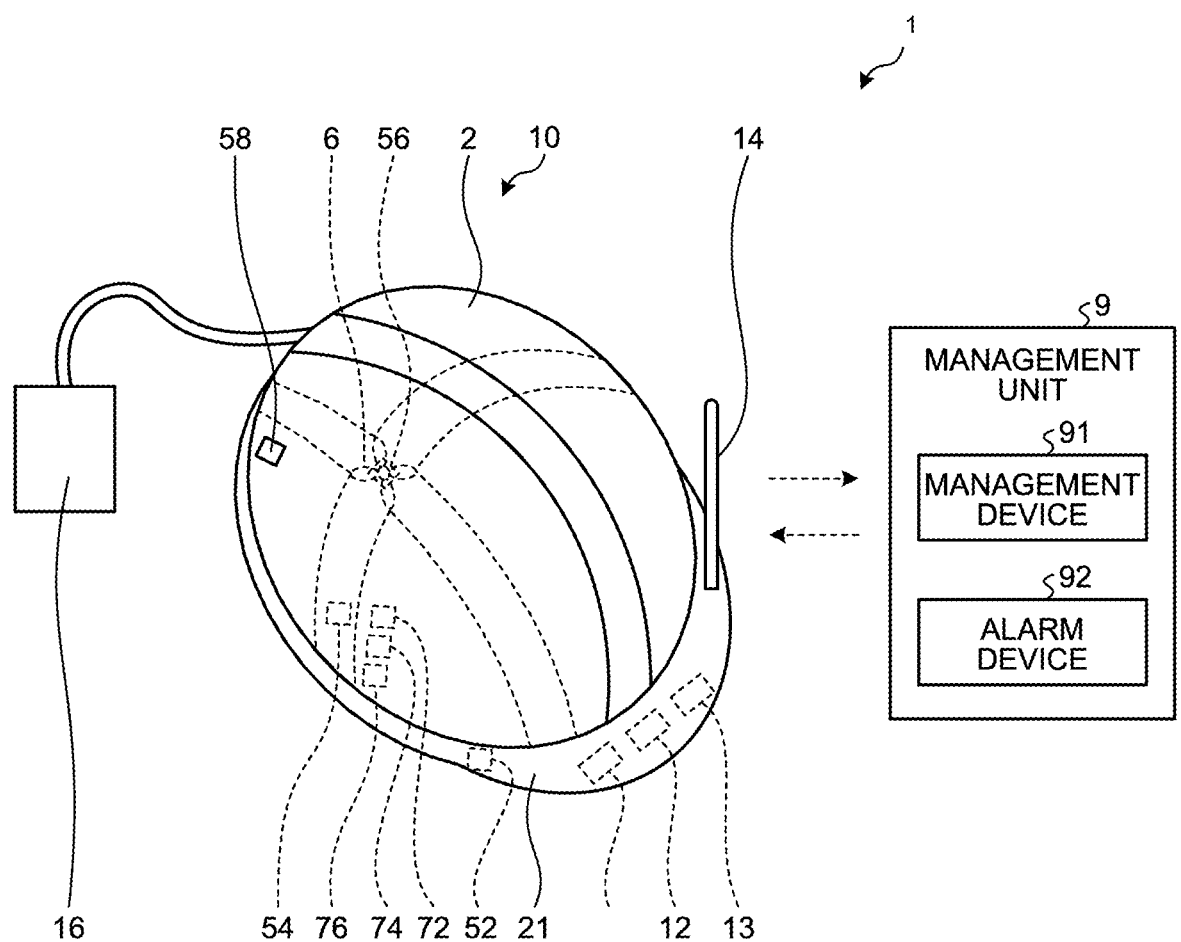
FIG. 1 is a schematic view of a heat stroke prevention system according to an embodiment.
Figure 2:
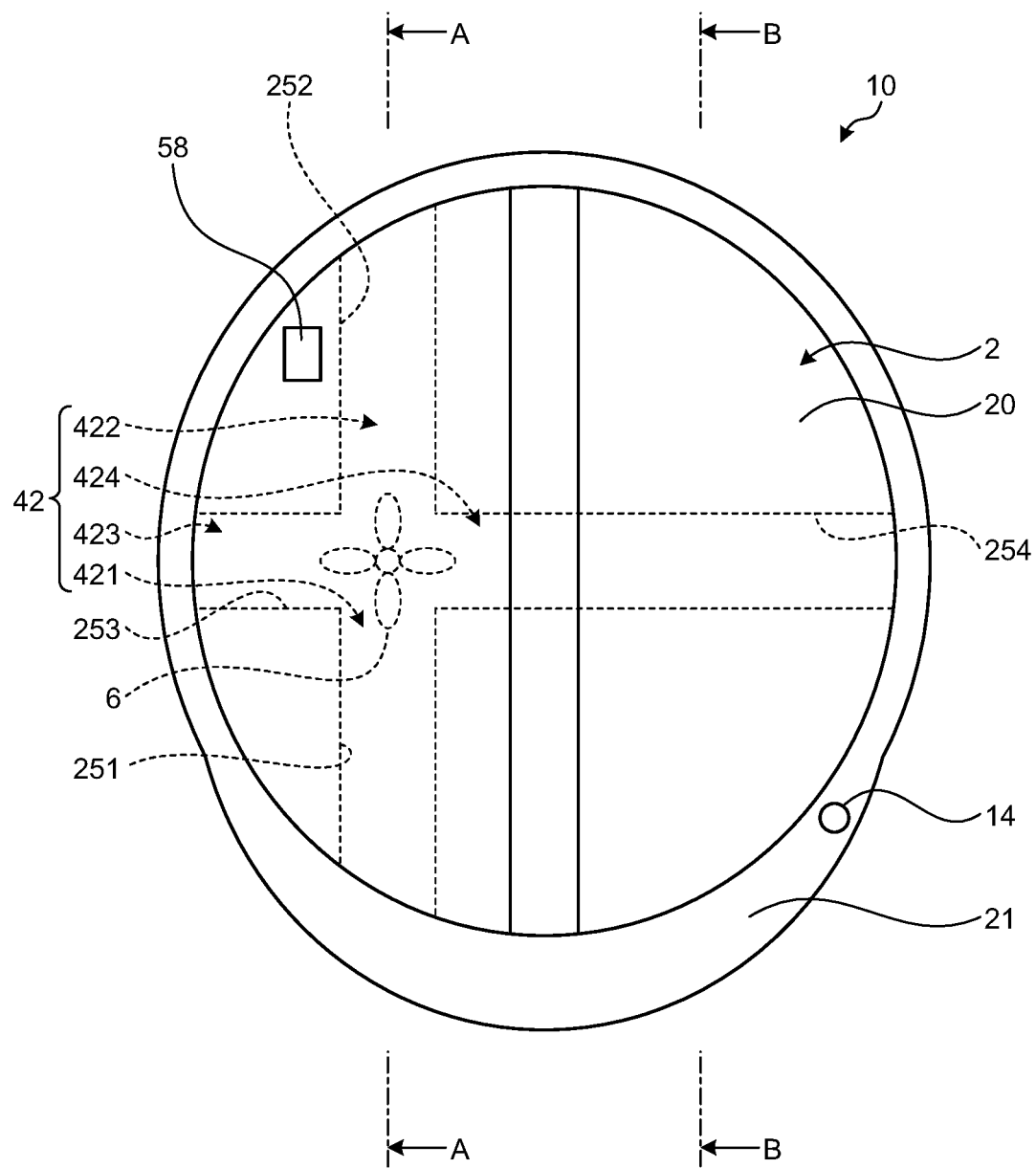
FIG. 2 is a plan view of a head-mounted device according to the embodiment.
Figure 3:
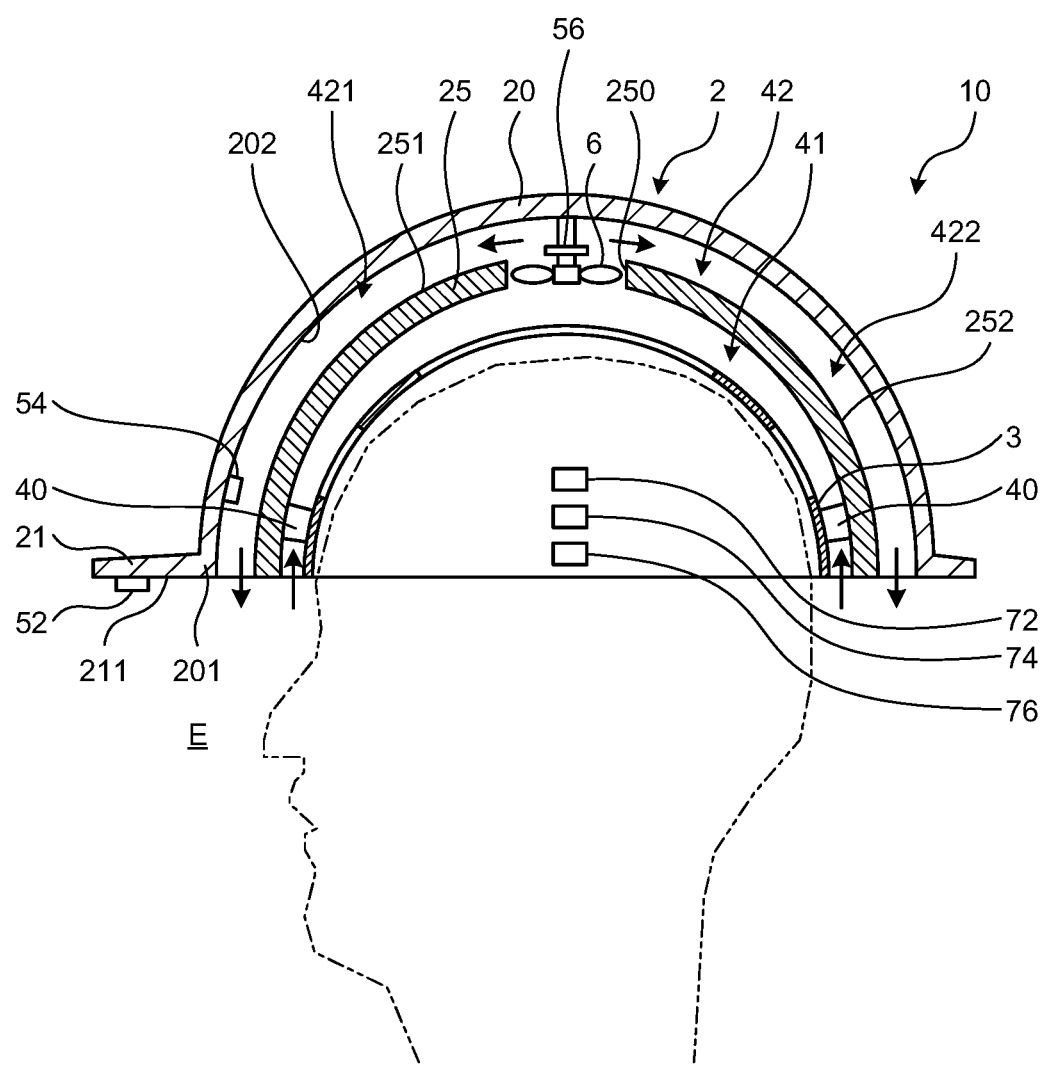
FIG. 3 is a cross-sectional view taken along the line A-A in FIG. 2.
Figure 4:
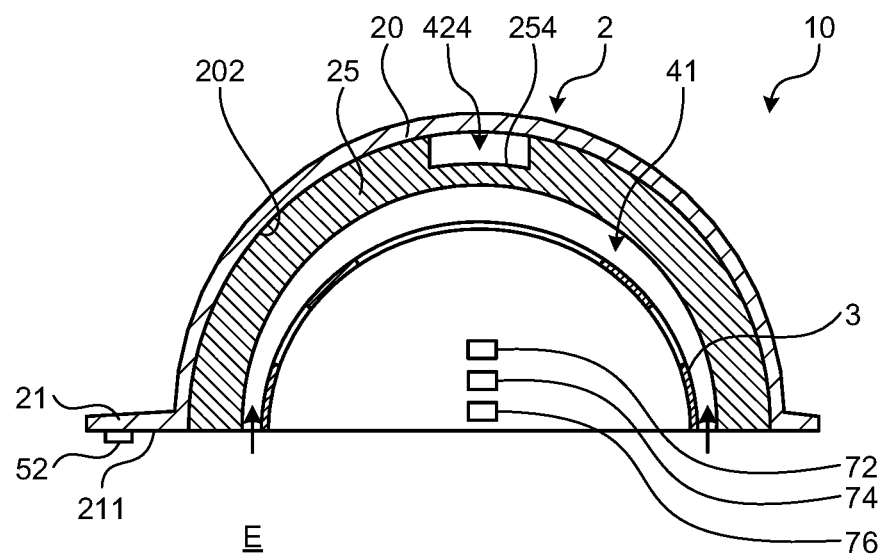
FIG. 4 is a cross-sectional view taken along the line B-B in FIG. 2.

FIG. 1 is a schematic view of a heat stroke prevention system according to an embodiment. FIG. 2 is a plan view of a head-mounted device according to the embodiment. FIG. 3 is a cross-sectional view taken along the line A-A in FIG. 2. FIG. 4 is a cross-sectional view taken along the line B-B in FIG. 2.

A heat stroke prevention system 1 according to the present embodiment is a system for suppressing the onset of heat stroke of a worker. For example, the heat stroke prevention system 1 is applied to a worker at a construction site. The heat stroke prevention system 1 also serves as a rehydration warning system 1 that warns the worker to be rehydrated, instructing a worker to be rehydrated, or promoting or instructing a worker to have a break. As illustrated in FIG. 1, the heat stroke prevention system 1 includes a head-mounted device 10 and a management unit 9.

The head-mounted device 10 is a device to be mounted to the head of a worker. In the following description, a human who wears the head-mounted device 10 is referred to as "wearer". For example, the head-mounted device 10 according to the present embodiment is a helmet. As illustrated in FIG. 1 to FIG. 4, the head-mounted device 10 includes an inner shell 3, an outer shell 2, a spacer 40, a fan 6, a battery 16, a first channel 41, a second channel 421, a second channel 422, a second channel 423, a second channel 424, a first humidity sensor 52, a second humidity sensor 54, an airflow sensor 56, an environmental sensor 58, a salinity sensor 72, a body temperature sensor 74, a heartbeat sensor 76, a control device 11, a alarm device 12, a communication device 13, and an antenna 14. In the following description, the second channel 421, the second channel 422, the second channel 423, and the second channel 424 are collectively referred to as "second channel 42" unless otherwise distinguished.

As illustrated in FIG. 3, the inner shell 3 is a member to face the head of a wearer. For example, the inner shell 3 is made of synthetic resin or cloth. The inner shell 3 has a plurality of gaps, and covers a part of the head of the wearer. Sweat caused from the head of the wearer becomes water vapor, and passes through the inner shell 3 without being blocked by the inner shell 3. The inner shell 3 may cover the whole of the head, and in such a case, the inner shell 3 is made of a material having moisture permeability.

As illustrated in FIG. 3, the outer shell 2 is a member covering the inner shell 3, and is semispherical. The outer shell 2 includes a main body 20, a flange 21, and a buffer 25. For example, the main body 20 is made of synthetic resin. The flange 21 is formed integrally with the main body 20, and protrudes from a lower end portion 201 of the main body 20 in a direction away from the wearer. The buffer 25 is attached to an inner surface 202 of the main body 20. The inner surface of the buffer 25 faces the inner shell 3. For example, the buffer 25 is made of polystyrene foam. It is preferred that the buffer 25 be made of a material having closed cells. In this manner, the passage of water vapor through the buffer 25 is suppressed. In the following description, a region outside a substantially semispherical region surrounded by the outer shell 2 is referred to as "outside E".

As illustrated in FIG. 2 to FIG. 4, the buffer 25 includes a recess 250, a recess 251, a recess 252, a recess 253, and a recess 254. The recess 250 is a hole provided in the inner surface of the buffer 25. The recess 251, the recess 252, the recess 253, and the recess 254 are grooves provided in the outer surface of the buffer 25, and extend from the recess 250 toward an end portion of the main body 20 along the main body 20.

As illustrated in FIG. 3, the spacer 40 is disposed between the inner shell 3 and the outer shell 2. More specifically, the spacer 40 is sandwiched between the inner shell 3 and the buffer 25. Thus, there is a gap between the inner shell 3 and the buffer 25.

As illustrated in FIG. 3, the fan 6 is provided on the outer shell 2. The fan 6 is disposed in the recess 250 of the buffer 25. For example, in the present embodiment, the fan 6 guides air located on the inner shell 3 side with respect to the buffer 25 toward the main body 20. In other words, the fan 6 moves the air from the lower side to the upper side. The air volume of the fan 6 is measured by the airflow sensor 56. The fan 6 can be adjusted manually or by a control circuit included in the control device 11 described later so that the air volume becomes a predetermined value. The fan 6 is adjusted to send air with an air volume so that the temperature of exhaust air exiting from the second channel 42 is equal to or higher than the dew-point temperature of exhaust air. In other words, the fan 6 is adjusted to send air at an air volume with which no condensation is caused around the exhaust air. The minimum air volume of the fan 6 is preferably an air volume with which the exhaust air is equal to or higher than the dew-point temperature. This is because, in general, a humidity sensor cannot measure the humidity of air having relative humidity higher than 100% (humidity of air having a dew-point temperature or less). In order to set the relative humidity of exhaust air to be 100% or less, the control device 11 may increase the air volume of the fan 6 such that temperature measured by the second humidity sensor 54, which will be described later, is equal to or higher than the dew-point temperature. In using under general working environments where the relative humidity of exhaust air does not reach 100% (under an environment where no condensation is caused around exhaust air), even when the air volume of the fan 6 is simply and manually set to the desired air volume in accordance with the tolerance of the wearer to hotness and the amount of sweating, the exhaust air becomes equal to or higher than the dew point. Thus, the second humidity sensor 54, which will be described later, can accurately measure the absolute humidity. The minimum air volume of the fan 6 is preferably 0.01 L/min or more so that air on the surface of the second humidity sensor 54 is replaced. The air volume of the fan 6 is more preferably 0.01 L/min or more and 500 L/min or less.

The battery 16 supplies power to the fan 6, the first humidity sensor 52, the second humidity sensor 54, the body temperature sensor 74, the heartbeat sensor 76, the environmental sensor 58, the control device 11, the alarm device 12, the communication device 13, and the antenna 14. The control device 11, the alarm device 12, the communication device 13, and the antenna 14 may be integrally formed on a substrate.

As illustrated in FIG. 3, the first channel 41 is a gap between the head of a wearer and the buffer 25. A lower end portion of the first channel 41 is connected to the outside E. An upper end portion of the first channel 41 is connected to the recess 250 in the buffer 25. Thus, the fan 6 is located at the upper end portion of the first channel 41. In other words, the fan 6 is located at a downstream end portion of the first channel 41.

As illustrated in FIGS. 2 to 4, the second channel 42 is a channel provided in the outer shell 2. The second channel 421 is a gap between the main body 20 and the recess 251 in the buffer 25. The second channel 422 is a gap between the main body 20 and the recess 252. The second channel 423 is a gap between the main body 20 and the recess 253. The second channel 424 is a gap between the main body 20 and the recess 254. A lower end portion of the second channel 42 is connected to the outside E. An upper end portion of the second channel 42 is connected to the recess 250 in the buffer 25. Thus, the first channel 41 is connected to the second channel 42 through the recess 250.

The fan 6 sends air from the first channel 41 toward the second channel 42. Air enters the first channel 41 from the outside E, and is discharged from the second channel 42 to the outside E. When the wearer sweats, water vapor is supplied to the first channel 41. Air in the first channel 41 including water vapor by sweat is discharged to the outside E through the second channel 42.

The first humidity sensor 52 is a sensor configured to measure an absolute humidity (hereinafter referred to as "first absolute humidity") of intake air entering the first channel 41. The absolute humidity is the amount of water vapor included in air per unit volume. As illustrated in FIG. 3, the first humidity sensor 52 is located on the outside E. For example, the first humidity sensor 52 is attached to an inner surface 211 (lower surface) of the flange 21. The first humidity sensor 52 measures the temperature and relative humidity of air of the outside E.

The second humidity sensor 54 is a sensor configured to measure an absolute humidity (hereinafter referred to as "second absolute humidity") of exhaust air exiting from the second channel 42. As illustrated in FIG. 3, the second humidity sensor 54 is located in the second channel 42. In other words, the second humidity sensor 54 is located downstream of the fan 6. For example, the second humidity sensor 54 is attached to the inner surface 202 of the main body 20 that faces the second channel 421. The second humidity sensor 54 measures the temperature and relative humidity of air in the second channel 421.

The airflow sensor 56 is a sensor configured to measure the air volume of the fan 6. As illustrated in FIG. 3, the airflow sensor 56 is attached to the air outlet of the fan 6. The airflow sensor 56 may be attached to the air inlet of the fan 6. The airflow measurement device that measures the air volume of the fan 6 is not limited to the airflow sensor 56. The airflow measurement device may include a pressure sensor configured to measure a differential pressure of the fan 6. The air volume of the fan 6 is calculated by the control device 11, which will be described later, based on information obtained from the pressure sensor. The airflow measurement device may include a detection mechanism configured to detect power supply voltage that drives the fan 6. The air volume of the fan 6 is calculated by the control device 11, which will be described later, based on information obtained from the detection mechanism.

The environmental sensor 58 is a sensor configured to measure a wet-bulb temperature, a dry-bulb temperature, and a black-bulb temperature around the wearer. As illustrated in FIG. 1, the environmental sensor 58 is attached to the outer surface of the outer shell 2.

The salinity sensor 72 is a sensor configured to measure salt concentration of the sweat of the wearer. As illustrated in FIG. 3, the salinity sensor 72 is attached to the inner surface of the inner shell 3. The salinity sensor 72 is in contact with the wearer. It is preferred that the salinity sensor 72 be in contact with the skin of the wearer. It is more preferred that the salinity sensor 72 be attached so as to be in contact with the forehead of the wearer.

The body temperature sensor 74 is a sensor configured to measure a body temperature of the wearer. As illustrated in FIG. 3, the body temperature sensor 74 is attached to the inner surface of the inner shell 3. The body temperature sensor 74 is in contact with the wearer. It is more preferred that the body temperature sensor 74 be capable of measuring a deep body temperature of the wearer. Examples of indices of the deep body temperature include oral temperature, rectal temperature, and eardrum temperature. In the case where the body temperature sensor 74 measures the deep body temperature, the mounting position of the body temperature sensor 74 is adjusted as appropriate.

The heartbeat sensor 76 is a sensor configured to measure the heart rate of the wearer. As illustrated in FIG. 3, the heartbeat sensor 76 is attached to the inner surface of the inner shell 3. The heartbeat sensor 76 is in contact with the wearer. It is preferred that the heartbeat sensor 76 be in contact with the temple of the wearer.

The control device 11 is a computer, and includes, for example, a central processing unit (CPU), read only memory (ROM), random access memory (RAM), an input interface, and an output interface. The control device 11 is electrically connected to the first humidity sensor 52, the second humidity sensor 54, the airflow sensor 56, the salinity sensor 72, the body temperature sensor 74, the heartbeat sensor 76, and the environmental sensor 58, and receives measured values. The control device 11 calculates medical parameters based on information obtained from the sensors. For example, the control device 11 calculates the amount of sweating as a medical parameter. It is preferred that the control device 11 calculate a fluctuation in amount of sweating, a fluctuation in deep body temperature, and a heartbeat interval. Furthermore, it is preferred that the control device 11 index working environments and the degree of dangerous of heat stroke of the wearer from information obtained from the above-described sensors and calculated medical parameters, and control the alarm device 12 or the communication device 13 based on the index. The control device 11 is electrically connected to the fan 6, and may control the air volume of the fan 6. The control device 11 is attached to the inner surface 211 of the flange 21 as illustrated in FIG. 1.

The control device 11 stores information on the wearer, such as the body weight, age, working location, and working process of the wearer. For example, the control device 11 can obtain information on the wearer stored in a management device 91 described later through the communication device 13. Alternatively, information on the wearer may be directly input to the control device 11 before working.

The control device 11 calculates a first absolute humidity based on the temperature and relative humidity of intake air received from the first humidity sensor 52. There are various kinds of approximations for estimating the absolute humidity from the relative humidity. In this case, the absolute humidity is estimated by the Tetens equation, which is relatively commonly used. When the first absolute humidity is X (g/m³), the temperature of intake air is $t_A$ (K), the relative humidity of intake air is $RH_A$ (%), and the saturation vapor pressure of intake air is $e_A$ (hPa), the control device 11 obtains X from Equations (1) and (2) described below.

$$e_A = 6.11 \times 10^{\frac{7.5 t_A}{(t_A + 237.3)}} \tag{1}$$

$$X = 217 \times \frac{e_A}{273.15 \times t_A} \times \frac{RH_A}{100} \tag{2}$$

The control device 11 calculates the mass of water entering the first channel 41 per unit time based on the first absolute humidity (X) and the air volume of the fan 6 received from the airflow sensor 56. When the mass of water entering the first channel 41 per unit time is A (g/min) and the air volume of the fan 6 is V (m³/min), the control device 11 obtains A from Equation (3) described below.

$$A = XV \tag{3}$$

The control device 11 calculates a second absolute humidity based on the temperature and relative humidity of exhaust air received from the second humidity sensor 54. When the second absolute humidity is Y (g/m³), the temperature of exhaust air is $t_B$ (K), the relative humidity of exhaust air is $RH_B$ (%), and the saturation vapor pressure of exhaust air is $e_B$ (hPa), the control device 11 obtains Y from Equations (4) and (5) described below.

$$e_B = 6.11 \times 10^{\frac{7.5 t_B}{(t_B + 237.3)}} \tag{4}$$

$$Y = 217 \times \frac{e_B}{273.15 \times t_B} \times \frac{RH_B}{100} \tag{5}$$

The control device 11 calculates the sum of the masses of water discharged from the second channel 421, the second channel 422, the second channel 423, and the second channel 424 per unit time based on the second absolute humidity (Y) and the air volume of the fan 6. When the sum of the masses of water is B (g/min), the control device 11 obtains B from Equation (6) described below.

$$B = YV \tag{6}$$

When the mass of water evaporated from the head of the wearer per unit time is C (g/min), the control device 11 obtains C from Equation (7) described below. In the following description, the mass (C) of water evaporated from the head of the wearer per unit time is referred to as "amount of sweating".

$$C = B - A \tag{7}$$

Figure 5:
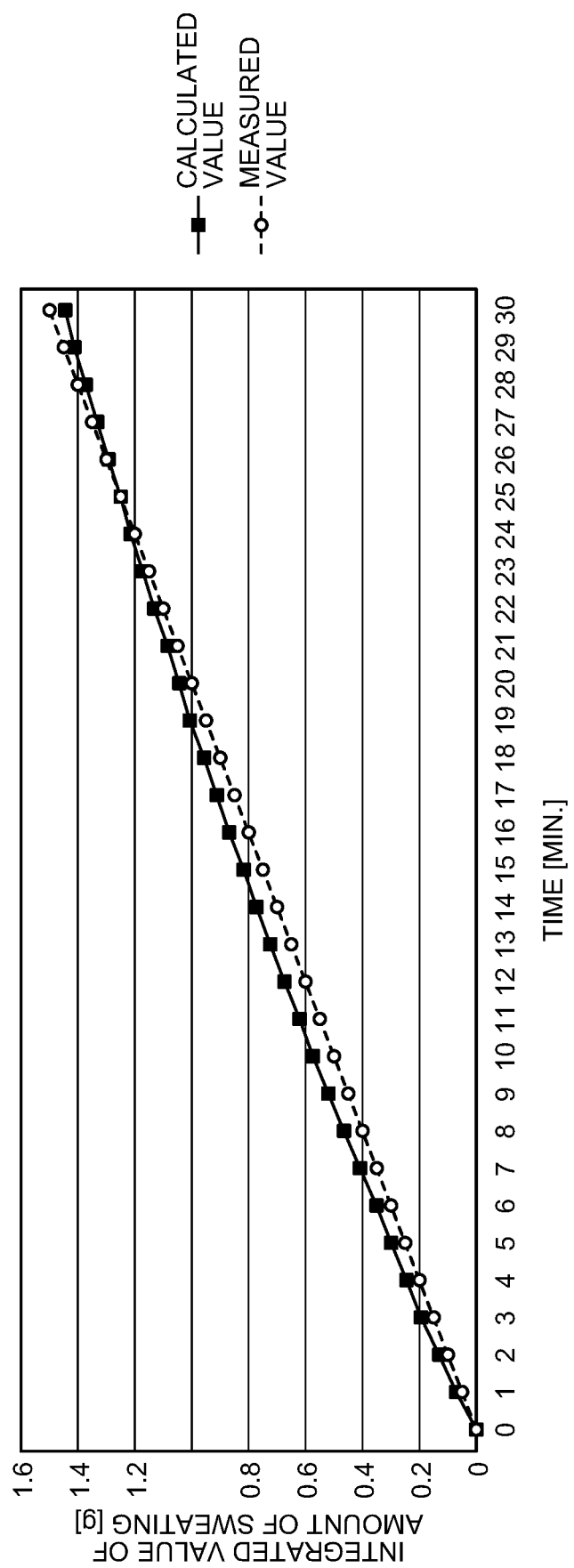
FIG. 5 is a graph illustrating an experimental result of comparing the amount of sweating calculated by a control device and the measured amount of sweating.

FIG. 5 is a graph illustrating the experimental result of comparing the amount of sweating calculated by the control device and the measured amount of sweating. An experiment to compare the amount of sweating calculated by the control device 11 by the above-mentioned method with the measured amount of sweating was performed by using a device (mannequin head) simulating the head of a human. The vertical axis in FIG. 5 is an integrated value (g) of the amount of sweating. The solid line in FIG. 5 indicates a transition of an integrated value (calculated value) of the amount of sweating calculated by the control device 11. The broken line in FIG. 5 indicates a transition of an integrated value (measured value) of the measured amount of sweating. The measured amount of sweating is the amount of sweating measured by using an electronic balance. As illustrated in FIG. 5, there is a small difference between the calculated value and the measured value. The control device 11 can calculate the amount of sweating with high accuracy. In order for the control device 11 to calculate the amount of sweating with high accuracy, it is desired to improve the accuracy of the air volume of the fan 6 and reduce noise of each sensor. In FIG. 5, the sweating substantial amount by time integration is displayed, but the sweating substantial amount per unit time may be displayed. In this manner, it is possible to determine a sign, such as the a high possibility of heat stroke, from an abnormal value indicating, for example, that the amount of sweating after a given period has increased abnormally.

The control device 11 calculates and stores the amount of sweating at predetermined intervals. The control device 11 determines whether the wearer is likely to suffer from heat stroke based on the transition of the amount of sweating. When the transition of the amount of sweating satisfies a predetermined condition, the control device 11 determines that the wearer is likely to suffer from heat stroke. For example, the control device 11 stores in advance a predetermined threshold for the amount of sweating, and when the amount of sweating exceeds the threshold, determines that the wearer is likely to suffer from heat stroke. Alternatively, the control device 11 stores in advance a predetermined threshold for the amount of sweating and a threshold count, and when the number of times the amount of sweating exceeds the threshold exceeds the threshold count, determines that the wearer is likely to suffer from heat stroke.

Alternatively, the control device 11 integrates the amount of sweating, and when the integrated amount of sweating exceeds a threshold, determines that the wearer is likely to suffer from heat stroke. The threshold in this case is, for example, the mass corresponding to 1.5% of the body weight of the wearer (see Non Patent Literature 1). The decrease amount of the body weight of the wearer can be measured by the amount of whole-body sweating of the wearer. To prevent heat stroke disease, it is preferred to use a value smaller than the above-mentioned threshold as the threshold. The control device 11 can calculate the amount of sweating of the head, and by storing in advance a correlation between the amount of sweating of the head and the amount of sweating of the whole body, can estimate the amount of whole-body sweating (decrease amount of body weight) from the amount of head sweating. Alternatively, the control device 11 stores in advance a threshold for the amount of sweating integrated in a predetermined period, and when the amount of sweating integrated in a predetermined period exceeds the threshold, determines that the wearer is likely to suffer from heat stroke. Alternatively, the control device 11 stores in advance a first threshold for the amount of sweating integrated in a predetermined period and a second threshold for wet-bulb temperature (or dry-bulb temperature) around the wearer, and determines the possibility that the wearer suffers from heat stroke based on the first threshold and the second threshold. For example, when the wet-bulb temperature exceeds the second threshold and the amount of sweating integrated in a predetermined period is lower than the first threshold, the control device 11 determines that the wearer is likely to suffer from heat stroke.

When the transition of the amount of sweating satisfies a predetermined condition, the control device 11 determines that the wearer needs to be rehydrated. For example, the control device 11 stores a predetermined threshold for the amount of whole-body sweating, and when the amount of whole-body sweating exceeds the threshold, determines that the wearer needs to be rehydrated. The control device 11 calculates the amount of water that the wearer should drink based on information on the amount of sweating. For example, the amount of water that the wearer should drink calculated by the control device 11 is the amount of water corresponding to the amount of whole-body sweating. The amount of water that the wearer should drink calculated by the control device 11 may be different from the amount of water corresponding to the amount of whole-body sweating.

The control device 11 calculates the amount of salt loss regarding the salt contained in the sweat evaporated from the head of the wearer per unit time based on the amount of sweating and the salt concentration of the sweat received from the salinity sensor 72. The control device 11 calculates and stores the amount of salt loss at predetermined intervals. The control device 11 determines whether the wearer is likely to suffer from heat stroke based on the transition of the amount of salt loss. When the transition of the amount of salt loss satisfies a predetermined condition, the control device 11 determines that the wearer is likely to suffer from heat stroke. For example, the control device 11 stores in advance a predetermined threshold for the amount of salt loss, and when the amount of salt loss exceeds the threshold, determines that the wearer is likely to suffer from heat stroke. Alternatively, the control device 11 stores in advance a predetermined threshold for the amount of salt loss and a threshold count, and when the number of times the amount of salt loss has exceeded the threshold exceeds the threshold count, determines that the wearer is likely to suffer from heat stroke. The control device 11 may store in advance an average salt concentration of sweat. The control device 11 may calculate the amount of salt loss for the wearer based on the average salt concentration of sweat. The average salt concentration of sweat is a predetermined value stored in the control device 11 in advance. The average salt concentration of sweat, for example, may be obtained from an average value of measurements of salt concentration of sweat measured for a predetermined number of times in advance for each wearer, or a generally known value of salt concentration may be used without using the salinity sensor 72. A generally known average salt concentration of sweat is 0.3% or more and 0.4% or less.

The control device 11 determines whether the wearer is likely to suffer from heat stroke based on a transition of body temperature. For example, the control device 11 determines that the wearer is likely to suffer from heat stroke when the body temperature received from the body temperature sensor 74 during the wearer's break does not return to the body temperature measured before the start of work (see Non Patent Literature 1).

The control device 11 determines whether the wearer is likely to suffer from heat stroke based on a transition of the heart rate. For example, the control device 11 determines that the wearer is likely to suffer from heat stroke when the state in which the heart rate per minute exceeds a value obtained by subtracting the age of the wearer from 180 continues for several minutes. Alternatively, the control device 11 determines that the wearer is likely to suffer from heat stroke when the heart rate per minute after one minute from a peak of activity of the wearer exceeds 120 (see Non Patent Literature 1).

The control device 11 calculates the wet-bulb globe temperature (WBGT) based on information measured by the environmental sensor 58. The control device 11 stores in advance a working process of the wearer, and hence grasps whether the wearer is outdoors or indoors. When the wearer is outdoors, the control device 11 calculates the wet-bulb globe temperature based on wet-bulb temperature, dry-bulb temperature, and black-bulb temperature. When the wearer is indoors, the control device 11 calculates the wet-bulb globe temperature based on wet-bulb temperature and black-bulb temperature. The control device 11 can also use the wet-bulb globe temperature for determination as to whether the wearer is likely to suffer from heat stroke.

The control device 11 may determine whether the wearer is likely to suffer from heat stroke by combining information obtained from the salinity sensor 72, the body temperature sensor 74, the heartbeat sensor 76, and the environmental sensor 58 with the amount of sweating.

The alarm device 12 is a device configured to allow the wearer to recognize that he/she is likely to suffer from heat stroke. The alarm device 12 is attached to the inner surface 211 of the flange 21 as illustrated in FIG. 1. When the control device 11 determines that the wearer is likely to suffer from heat stroke, the alarm device 12 issues an alarm. The type of alarm is not particularly limited. Examples of the alarm include sound, light, and vibration. The alarm device 12 is a device configured to allow the wearer himself/herself to recognize that he/she needs at least one of rehydration and salt supplementation. When the control device 11 determines that the wearer should take at least one of rehydration and salt supplementation, the alarm device 12 issues an alarm. The type of alarm is not particularly limited. Examples of the alarm include sound, light, and vibration. For example, when the control device 11 determines that the wearer should be supplied with at least one of water and salt, the alarm device 12 displays the amount of at least one of water and salt that the wearer should take calculated by the control device 11. For example, when the control device 11 determines that the wearer should take at least one of rehydration and salt supplementation, the alarm device 12 instructs, by voice, the wearer to drink water or take salt supplementation with the amount that the wearer should take calculated by the control device 11. In the alarm device 12, an instruction to take at least one of rehydration and salt supplementation may be used in combination with, for example, an instruction to prompt to have a break based on continuous working time.

The communication device 13 and the antenna 14 are devices configured to transmit information obtained by the control device 11 to the management unit 9. As illustrated in FIG. 1, the communication device 13 is attached to the inner surface 211 of the flange 21. As illustrated in FIG. 1, the antenna 14 is attached to the outer surface of the flange 21.

The management unit 9 is a place where a manager who monitors the wearer is located. As illustrated in FIG. 1, the management unit 9 includes a management device 91 and an alarm device 92. The management device 91 receives information from a plurality of head-mounted devices 10. The management device 91 stores information such as a working place, a working process, and age of a plurality of wearers.

The management device 91 stores the amount of sweating and the amount of salt loss obtained from the control device 11 and information obtained from each sensor. The management device 91 determines whether the wearer is likely to suffer from heat stroke based on the transitions of the amount of sweating, the amount of salt loss, the body temperature, the heart rate, and the heat index. The management device 91 determines whether the wearer should take at least one of rehydration and salt supplementation based on the transition of the amount of sweating, the amount of salt loss, the body temperature, the heart rate, and the heat index. A specific determination method may be the same as or different from the determination method in the control device 11.

The alarm device 92 is a device configured to allow a manager to recognize that the wearer is likely to suffer from heat stroke. When the management device 91 determines that the wearer is likely to suffer from heat stroke, the alarm device 92 issues an alarm to the manager. The alarm device 92 is a device configured to allow the manager to recognize that the wearer should take at least one of rehydration and salt supplementation. When the management device 91 determines that the wearer should take at least one of rehydration and salt supplementation, the alarm device 92 issues an alarm to the manager. Similarly to the alarm device 12, the type of alarm is not particularly limited. In the alarm device 92, an instruction to take at least one of rehydration and salt supplementation may be used in combination with, for example, an instruction to prompt to have a break based on continuous working time.

The materials of the inner shell 3 and the outer shell 2 are merely an example, and not particularly limited. The head-mounted device 10 does not necessarily have to include the inner shell 3. For example, the spacer 40 may be in contact with the head so that a gap is formed between the outer shell 2 and the head.

In the head-mounted device 10, air on the outside E does not necessarily have to enter from the first channel 41. The air on the outside E may enter from the second channel 42 and be discharged from the first channel 41. In such a case, it is preferred that the second humidity sensor 54 be disposed near an exit of the first channel 41.

Air may flow out or flow in through a hole opened to the outer surface of the outer shell 2. When air flows out from the hole opened to the outer surface of the outer shell 2, the second humidity sensor 54 may be disposed in the hole. When air flows in through the hole opened to the outer surface of the outer shell 2, the second humidity sensor 54 may be disposed at, for example, a lower end portion of the first channel 41. The first humidity sensor 52 may be disposed on the inner surface 211 of the flange 21. When air flows in through a hole opened to the outer surface of the outer shell 2, the first humidity sensor 52 may be disposed in the hole. When air flows out or in from the hole opened to the outer surface of the outer shell 2 in this way, the hole is the second channel.

The number of the second humidity sensors 54 included in the head-mounted device 10 does not necessarily have to be one. For example, the second humidity sensor 54 may be disposed in each of the second channel 421, the second channel 422, the second channel 423, and the second channel 424. In such a case, it is preferred that the control device 11 calculate the amount of sweating based on an average of measurement results of the second humidity sensors 54.

The head-mounted device 10 does not necessarily have to have a plurality of second channels 42, and may have at least one second channel 42. In other words, the head-mounted device 10 may have at least one of the second channel 421, the second channel 422, the second channel 423, and the second channel 424.

In the case where the air volume of the fan 6 is automatically adjusted by the control device 11, the control device 11 may increase the air volume of the fan 6 when the temperature of exhaust air becomes lower than the dew-point temperature. The control device 11 may increase the air volume of the fan 6 as the amount of sweating increases. The fan 6 may send air from the second channel 42 to the first channel 41.

The head-mounted device 10 does not necessarily have to include the airflow sensor 56, the body temperature sensor 74, the heartbeat sensor 76, and the environmental sensor 58. The head-mounted device 10 may include, instead of the airflow sensor 56, the pressure sensor configured to measure the differential pressure of the fan 6 or the detection mechanism configured to detect the power supply voltage that drives the fan 6. The head-mounted device 10 may measure the air volume in any desired way as long as it can measure the air volume of the fan 6. In the present embodiment, the head-mounted device 10 sets the air volume of a measurement value measured by the airflow measurement device as V ($m^3$/min), but may set the air volume of the setting value set by the control device 11 as V ($m^3$/min). In other words, the head-mounted device 10 does not need to measure the air volume of the fan 6. The head-mounted device 10 may include at least the salinity sensor 72, the first humidity sensor 52, and the second humidity sensor 54, as sensors. The first humidity sensor 52 and the second humidity sensor 54 do not necessarily have to be sensors configured to measure temperature and relative humidity, as long as they can measure absolute humidity. For example, the first humidity sensor 52 and the second humidity sensor 54 may be a moisture meter (infrared moisture meter) using light (near-infrared light). Moisture has property of absorbing near-infrared light of a specific wavelength. An infrared moisture meter measures absolute humidity based on the magnitude of absorbance. The first humidity sensor 52 does not necessarily have to be disposed on the inner surface 211, and, for example, may be disposed on the inner surface of the buffer 25. When the fan 6 sends air from the second channel 42 to the first channel 41, the first humidity sensor 52 may be disposed on the inner surface 202. In this case, for example, the second humidity sensor 54 is disposed on the inner surface of the buffer 25.

The head-mounted device 10 may include a sensor other than the above-mentioned sensors. For example, the head-mounted device 10 may include a cerebral blood flow sensor configured to measure the cerebral blood flow of a wearer. As a cerebral blood flow sensor, a device configured to measure brain functions in a non-invasive manner from the scalp by using near-infrared light has been known. Such a device is called near infrared spectroscopy (NIRS). The head-mounted device 10 may include an acceleration sensor. In this manner, the head-mounted device 10 can detect dizziness of the wearer.

The head-mounted device 10 does not necessarily have to include the communication device 13 and the antenna 14. Even in such a case, the head-mounted device 10 includes the alarm device 12, and hence the wearer can recognize that he/she is likely to suffer from heat stroke.

The head-mounted device 10 does not necessarily have to include the control device 11. In such a case, information measured by the first humidity sensor 52, the second humidity sensor 54, the airflow sensor 56, the salinity sensor 72, the body temperature sensor 74, the heartbeat sensor 76, and the environmental sensor 58 is transmitted to the management device 91 through the communication device 13. The management device 91 calculates the amount of sweating based on Equations (1) to (7) described above, and determines whether the wearer is likely to suffer from heat stroke. Even when the head-mounted device 10 includes the control device 11, the management device 91 may calculate the amount of sweating.

The control device 11 and the management device 91 may accumulate information measured by each sensor in the past, and change a determination criterion as to whether the wearer is likely to suffer from heat stroke based on the information. The control device 11 and the management device 91 may have artificial intelligence (AI). By learning accumulated information with the artificial intelligence, the accuracy of determination as to whether the wearer is likely to suffer from heat stroke can be improved.

The head-mounted device 10 does not necessarily have to include the alarm device 12. The management unit 9 does not necessarily have to include the alarm device 92. It is preferred that the heat stroke prevention system 1 have at least one of the alarm device 12 and the alarm device 92.

As described above, the head-mounted device 10 includes the outer shell 2, the first channel 41, the second channel 42, the fan 6, the salinity sensor 72, the first humidity sensor 52, and the second humidity sensor 54. The first channel 41 is a gap between the head of a wearer and the outer shell 2. The second channel 42 is provided in the outer shell 2 and connected to the first channel 41. The fan 6 sends air from one of the first channel 41 and the second channel 42 to the other. The salinity sensor 72 is a device configured to measure the salt concentration of the sweat of the wearer. The first humidity sensor 52 is a device configured to measure an absolute humidity of intake air entering one of the first channel 41 and the second channel 42. The second humidity sensor 54 is a device configured to measure an absolute humidity of exhaust air exiting from the other of the first channel 41 and the second channel 42.

As a result, the head-mounted device 10 can obtain the amount of sweating and the amount of salt loss of the head of the wearer based on information obtained from the salinity sensor 72, the first humidity sensor 52, and the second humidity sensor 54. As a result, the head-mounted device 10 can more highly accurately measure the physical conditions of the wearer as a worker that are necessary for estimating the possibility of heat stroke.

In the head-mounted device 10, the fan 6 sends air with an air volume with which the temperature of exhaust air becomes equal to or higher than a dew-point temperature of the exhaust air.

As a result, the relative humidity of exhaust air becomes less than 100%. Condensation by water included in the exhaust air is suppressed. Thus, the accuracy of the absolute humidity obtained by the second humidity sensor 54 is improved. As a result, the head-mounted device 10 can improve the accuracy of measurement of the amount of sweating.

In the head-mounted device 10, the first humidity sensor 52 is located on the outside E of the outer shell 2.

As a result, the first humidity sensor 52 is less affected by water vapor caused by the sweat of the wearer. Thus, the accuracy of the absolute humidity obtained by the first humidity sensor 52 is improved.

In the head-mounted device 10, the first humidity sensor 52 measures temperature and relative humidity of intake air, and is located on the inner surface (for example, inner surface 211) of the outer shell 2.

As a result, the outer shell 2 blocks the sunlight, which makes it different for the first humidity sensor 52 to be exposed to the sunlight. Since the temperature of intake air measured by the first humidity sensor 52 is less likely to have an error, the accuracy of the absolute humidity obtained by the first humidity sensor 52 is improved.

In the head-mounted device 10, the fan 6 sends air from the first channel 41 toward the second channel 42, and is located at a downstream end portion of the first channel 41. The second humidity sensor 54 is located downstream of the fan 6.

As a result, air including water vapor caused by sweat is agitated by the fan 6, so that the distribution of the absolute humidity on the downstream side of the fan 6 tends to be uniform. When a plurality of the second channels 42 are provided, the difference in absolute humidity among the second channels 42 is suppressed. Thus, the accuracy of the absolute humidity obtained by the second humidity sensor 54 is improved.

The head-mounted device 10 includes the body temperature sensor 74 configured to measure a body temperature of the wearer. As a result, the head-mounted device 10 can more highly accurately measure the physical conditions of the wearer.

In the head-mounted device 10, the body temperature sensor 74 measures a deep body temperature. As a result, the head-mounted device 10 can more highly accurately measure the physical conditions of the wearer.

The head-mounted device 10 includes the heartbeat sensor 76 configured to measure a heart rate of the wearer. As a result, the head-mounted device 10 can more highly accurately measure the physical conditions of the wearer.

The head-mounted device 10 includes the environmental sensor 58 configured to measure a wet-bulb temperature and a black-bulb temperature around the wearer. As a result, the head-mounted device 10 can more highly accurately measure the physical conditions of the wearer.

The head-mounted device 10 further includes an airflow measurement device configured to measure the air volume of the fan 6. As a result, the air volume can be corrected by real-time measurement. Because the amount of sweating of the head of the wearer can be calculated based on more accurate airflow value, the amount of sweating of the head of the wearer can be obtained more suitably. As a result, the head-mounted device 10 can more highly accurately measure the physical conditions of the wearer as a worker that are necessary for estimating the possibility of heat stroke.

Furthermore, in the head-mounted device 10, the airflow measurement device is an airflow sensor 56 provided at the air inlet or the air outlet of the fan 6. As a result, the air volume of the fan 6 can be easily measured.

The head-mounted device 10 may include, instead of the airflow sensor 56, the pressure sensor configured to measure the differential pressure of the fan 6, and the control device 11 configured to calculate the air volume of the fan 6 based on the information obtained from the pressure sensor. As a result, the air volume of the fan 6 can be easily measured.

Furthermore, the head-mounted device 10 may include, instead of the airflow sensor 56, a detection mechanism configured to detect power supply voltage that drives the fan 6, and the control device 11 configured to calculate the air volume of the fan 6 based on information obtained from the detection mechanism. As a result, the air volume of the fan 6 can be easily measured.

The head-mounted device 10 includes the control device 11 and the alarm device 12. The control device 11 calculates an amount of sweating and the amount of salt loss of the wearer based on information obtained from the salinity sensor 72, the first humidity sensor 52, and the second humidity sensor 54. The alarm device 12 issues an alarm when a transition of the amount of sweating satisfies a predetermined condition.

Since a large amount of sweating is an initial symptom of heat stroke (see Non Patent Literature 2), the head-mounted device 10 can detect whether the wearer has an initial symptom of heat stroke. In other words, the head-mounted device 10 can detect heat stroke at an early stage. The head-mounted device 10 can improve the accuracy of estimation of the possibility of heat stroke. The alarm device 12 allows the wearer to recognize at an early stage that he/she may suffer from heat stroke. Thus, the head-mounted device 10 can suppress severe heat stroke.

The heat stroke prevention system 1 includes the head-mounted device 10 and the management device 91. The head-mounted device 10 includes the communication device 13 configured to transmit, through wireless communication, information obtained from the salinity sensor 72, the first humidity sensor 52, and the second humidity sensor 54. The management device 91 receives the information from the communication device 13, and stores the amount of sweating and the amount of salt loss of the wearer.

As a result, the management device 91 can detect whether the wearer at a remote location has an initial symptom of heat stroke. In other words, the heat stroke prevention system 1 can detect heat stroke at an early stage. The heat stroke prevention system 1 can improve the accuracy of estimation of the possibility of heat stroke. The manager can recognize, through the management device 91, that the wearer may suffer from heat stroke. Thus, the heat stroke prevention system 1 can suppress severe heat stroke.

The heat stroke prevention system 1 includes the alarm device 92 configured to issue an alarm to the manager when a transition of at least one of the amount of sweating and the amount of salt loss satisfies a predetermined condition.

As a result, the manager can early recognize that the wearer may suffer from heat stroke. Thus, severe heat stroke is suppressed.

In the heat stroke prevention system 1, the head-mounted device 10 includes the alarm device 12 configured to issue an alarm to the wearer when a transition of at least one of the amount of sweating and the amount of salt loss satisfies a predetermined condition.

As a result, the wearer can early recognize that he/she may suffer from heat stroke. Thus, severe heat stroke is suppressed.

The rehydration warning system 1 includes the head-mounted device 10 and the management device 91. The head-mounted device 10 includes the communication device 13 configured to transmit, by wireless communication, information obtained from the salinity sensor 72, the first humidity sensor 52, and the second humidity sensor 54. The management device 91 receives information from the communication device 13, and stores and displays the amount of sweating of the wearer.

As a result, the management device 91 can detect whether the wearer at a remote location needs at least one of rehydration and salt supplementation. The manager can recognize, through the management device 91, that the wearer needs at least one of rehydration and salt supplementation, and can instruct the wearer to take at least one of water and salt or to have a break. Thus, the rehydration warning system 1 can prevent heat stroke disease caused by the decrease in at least one of water and salt in the body of the wearer due to sweating. The rehydration warning system 1 contributes to safe labor management of a wearer who wears the head-mounted device 10.

The rehydration warning system 1 includes the alarm device 92 configured to issue an alarm to the manager when a transition of at least one of the amount of sweating and the amount of salt loss satisfies a predetermined condition.

As a result, the manager can early recognize that the wearer needs at least one of rehydration and salt supplementation. Thus, it is possible to prevent heat stroke disease caused by the decrease in at least one of water and salt in the body of the wearer due to sweating.

In the rehydration warning system 1, the head-mounted device 10 includes the alarm device 12 configured to issue an alarm to the wearer when a transition of at least one of the amount of sweating and the amount of salt loss satisfies a predetermined condition.

As a result, the wearer can recognize at an early stage that he/she is in a state where at one of rehydration and salt supplementation is needed due to the decrease in at least one of water and salt in the body due to sweating. This allows the wearer to spontaneously take at least one of rehydration and salt supplementation with an appropriate amount, or have a break. Thus, it is possible to prevent heat stroke disease caused by the decrease in at least one of water and salt in the body of the wearer due to sweating. In the rehydration warning system 1, an instruction from the manager by using the alarm device 92 to take at least one of rehydration and salt supplementation, and an instruction for the wearer to spontaneously take at least one of rehydration and salt supplementation, by using the alarm device 12 may be used in combination.

Modification

Figure 6:
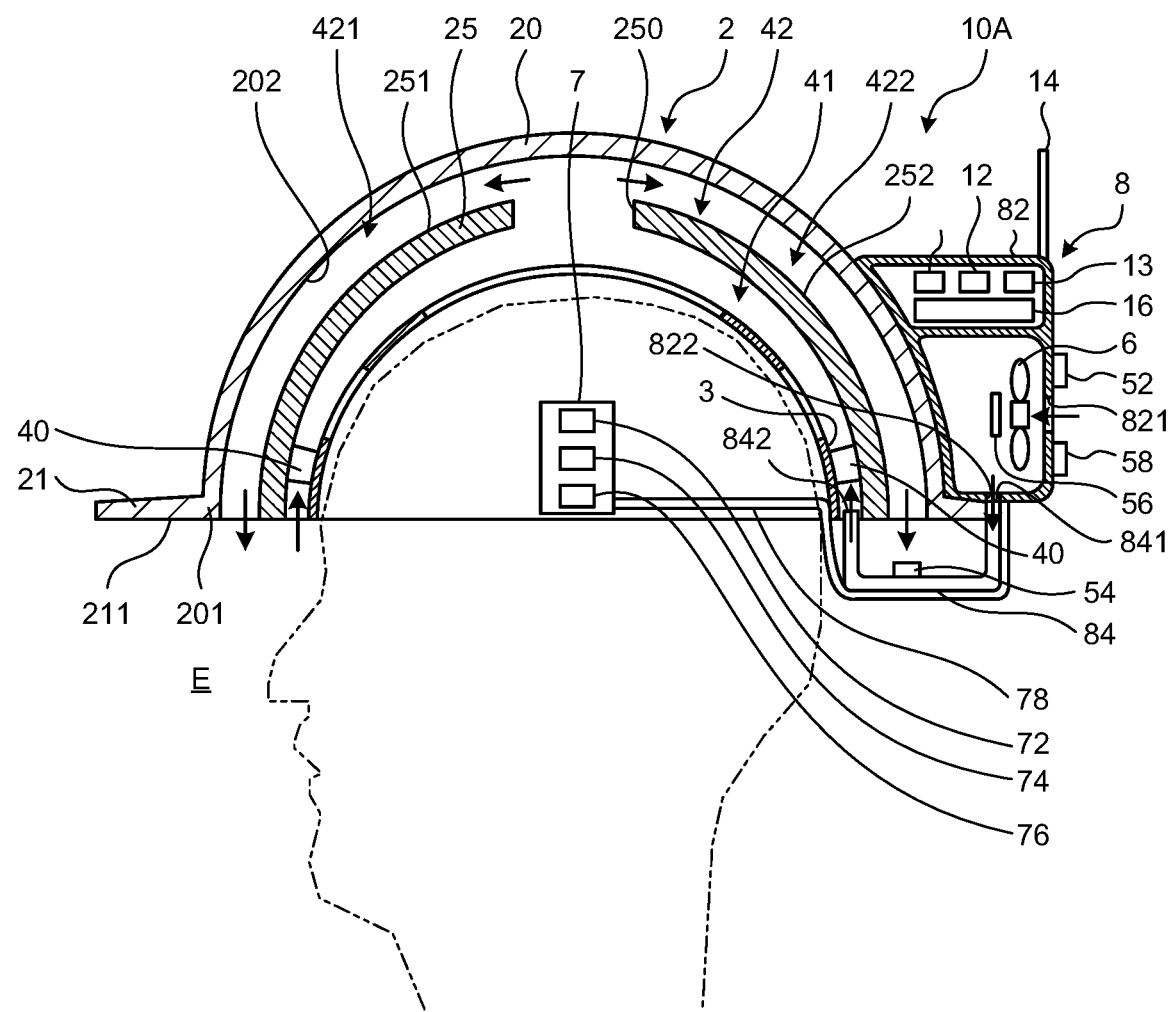
FIG. 6 is a schematic cross-sectional view of a modification of the head-mounted device.

FIG. 6 is a schematic cross-sectional view of a modification of the head-mounted device. In the head-mounted device 10A of the modification, the same reference numerals will be applied to the same configuration as the above-described head-mounted device 10 and explanation will be omitted, and a different configuration will be explained. Compared to the head-mounted device 10, the head-mounted device 10A of the modification differs therefrom in that it includes a sensor unit 8. Compared to the head-mounted device 10, the head-mounted device 10A of the modification differs therefrom in that the fan 6, the first humidity sensor 52, the second humidity sensor 54, the airflow sensor 56, the environmental sensor 58, the salinity sensor 72, the body temperature sensor 74, the heartbeat sensor 76, the control device 11, the alarm device 12, the communication device 13, the antenna 14, and the battery 16 are provided in the sensor unit 8. The sensor unit 8 includes a housing 82, a tube member 84, and a subunit 7.

The housing 82 is attached to the outer surface of the outer shell 2. The housing 82 has an intake port 821 to intake air, and a blast port 822 to send out air. Outside the housing 82, the first humidity sensor 52, the environmental sensor 58, and the antenna 14 are attached in the vicinity of the intake port 821. Inside the housing 82, the fan 6, the airflow sensor 56, the control device 11, the alarm device 12, the communication device 13, and the battery 16 are mounted. In the modification, the airflow sensor 56 is attached to the air outlet of the fan 6. The airflow sensor 56 may be attached to the air inlet of the fan 6.

One end 841 of the tube member 84 is disposed on the outside E of the head-mounted device 10A. The other end 842 of the tube member 84 is disposed inside the head-mounted device 10A. The one end 841 of the tube member 84 is connected to the blast port 822 of the housing 82. The other end 842 of the tube member 84 is disposed at the lower end of the first channel 41. Outside the tube member 84, the second humidity sensor 54 is attached in the vicinity of the lower end of the second channel 42. The other end 842 of the tube member 84 may be disposed at the lower end of the second channel 42.

The subunit 7 is, for example, a plate-shaped member. The salinity sensor 72, the body temperature sensor 74, and the heartbeat sensor 76 are mounted on one surface of the subunit 7. The subunit 7 is attached to the inner surface of the inner shell 3 such that a surface on which the salinity sensor 72, body temperature sensor 74 and heartbeat sensor 76 are mounted is on the inside. The subunit 7 is connected to the housing 82. In the modification, the subunit 7 is connected to the housing 82 with a cable 78.

It is preferred that the housing 82 be detachable from the outer shell 2. It is preferred that the subunit 7 be detachable from the inner shell 3. It is preferred that the sensor unit 8 be detachable from the outer shell 2 and the inner shell 3.

As described above, the head-mounted device 10A includes the sensor unit 8. The sensor unit 8 includes the housing 82, the tube member 84, the fan 6, the salinity sensor 72, the first humidity sensor 52 and the second humidity sensor 54. The tube member 84 connects respective ends of upstream sides of the first channel 41 and the second channel 42 to the fan 6. The tube member 84, the fan 6, the salinity sensor 72, the first humidity sensor 52 and the second humidity sensor 54 are supported by the housing 82.

As a result, for example, by attaching the sensor unit 8 to the outer shell 2, it is possible to obtain the amount of sweating of the head of the wearer based on information obtained from the first humidity sensors 52 and the second humidity sensor 54. The head-mounted device 10A can more easily measure the physical conditions of the wearer as a worker that are necessary for estimating the possibility of heat stroke.

In the head-mounted device 10A, the sensor unit 8 is detachable from the outer shell 2. Thus, the outer shell 2 can be cleaned with water, for example.

REFERENCE SIGNS LIST

1 Heat stroke prevention system, rehydration warning system
10, 10A Head-mounted device
11 Control device
12 Alarm device
13 Communication device
14 Antenna
16 Battery
2 Outer shell
20 Main body
201 Lower end
202 Inner surface
21 Flange
211 Inner surface
25 Buffer
250, 251, 252, 253, 254 Recesses
3 Inner shell
40 Spacer
41 First channel
42, 421, 422, 423, 424 Second channel
52 First humidity sensor
54 Second humidity sensor
56 Airflow sensor
58 Environmental sensor
6 Fan
7 Subunit
72 Salinity sensor
74 Body temperature sensor 76 Heartbeat sensor
78 Cable
8 Sensor unit
82 Housing
821 Intake port
822 Blast port
84 Tube member
841 One end
842 Other end
9 Management unit
91 Management device
92 Alarm device
E Outside

The invention claimed is:

1. A head-mounted device, comprising:
an inner shell to face a head of a wearer;
an outer shell covering the inner shell;
a first channel as a gap between the inner shell and the outer shell;
a second channel provided in the outer shell and connected to the first channel;
a fan configured to send air from one of the first channel and the second channel to the other;
a salinity sensor attached to an inner surface of the inner shell and configured to measure salt concentration of sweat of the wearer;
a first humidity sensor configured to measure an absolute humidity of intake air entering one of the first channel and the second channel;
a second humidity sensor configured to measure an absolute humidity of exhaust air exiting from the other of the first channel and the second channel; and
a control device configured to calculate an amount of sweating and an amount of salt loss of the wearer based on information obtained from the salinity sensor, the first humidity sensor, and the second humidity sensor.

2. The head-mounted device according to claim 1, wherein the fan sends air with an air volume with which a temperature of the exhaust air becomes equal to or higher than a dew-point temperature of the exhaust air.

3. The head-mounted device according to claim 1, wherein the first humidity sensor is located on outside of a region surrounded by the outer shell.

4. The head-mounted device according to claim 1, wherein
the fan sends air from the first channel toward the second channel, and is located at a downstream end portion of the first channel, and
the second humidity sensor is located downstream of the fan.

5. The head-mounted device according to claim 1, comprising:
a sensor unit including:
a housing;
a tube member having one end connected to the housing and another end disposed inside the outer shell;
the fan;
the salinity sensor;
the first humidity sensor; and
the second humidity sensor, wherein
the first humidity sensor and the fan are attached to the housing,
the second humidity sensor is attached to the tube member, and
the salinity sensor is connected to the housing.

6. The head-mounted device according to claim 5, wherein the sensor unit is detachable from the outer shell.

7. The head-mounted device according to claim 1, comprising a body temperature sensor configured to measure a body temperature of the wearer.

8. The head-mounted device according to claim 7, wherein the body temperature sensor measures a deep body temperature.

9. The head-mounted device according to claim 1, comprising a heartbeat sensor configured to measure a heart rate of the wearer.

10. The head-mounted device according to claim 1, comprising an environmental sensor configured to measure a wet-bulb temperature and a black-bulb temperature around the wearer.

11. The head-mounted device according to claim 1, comprising an airflow measurement device configured to measure an air volume of the fan.

12. The head-mounted device according to claim 1, comprising
an alarm device configured to issue an alarm when a transition of the amount of sweating satisfies a predetermined condition.

13. A heat stroke prevention system, comprising:
the head-mounted device according to claim 1; and
a management device, wherein
the head-mounted device includes a communication device configured to transmit, through wireless communication, information obtained from the salinity sensor, the first humidity sensor, and the second humidity sensor, and
the management device receives the information from the communication device and stores the amount of sweating and the amount of salt loss of the wearer.

14. The heat stroke prevention system according to claim 13, comprising an alarm device configured to issue an alarm to the wearer or a manager when a transition of at least one of the amount of sweating and the amount of salt loss satisfies a predetermined condition.

15. A rehydration warning system, comprising:
the head-mounted device according to claim 1; and
a management device, wherein
the head-mounted device includes a communication device configured to transmit, through wireless communication, information obtained from the salinity sensor, the first humidity sensor, and the second humidity sensor, and
the management device receives the information from the communication device and stores the amount of sweating and the amount of salt loss of the wearer.

16. The rehydration warning system according to claim 15, comprising an alarm device configured to issue an alarm to the wearer or a manager when a transition of at least one of the amount of sweating and the amount of salt loss satisfies a predetermined condition.

* * * * *